United States Patent
Jaffe et al.

(10) Patent No.: US 10,987,023 B2
(45) Date of Patent: Apr. 27, 2021

(54) SYSTEM AND METHOD FOR DETERMINING ONE OR MORE BREATHING PARAMETERS OF A SUBJECT

(75) Inventors: Michael Brian Jaffe, Cheshire, CT (US); Joseph Allen Orr, Park City, UT (US)

(73) Assignee: Koninklijke Philips N.V., Eindhoven (NL)

(*) Notice: Subject to any disclaimer, the term of this patent is extended or adjusted under 35 U.S.C. 154(b) by 649 days.

(21) Appl. No.: 13/993,159

(22) PCT Filed: Dec. 9, 2011

(86) PCT No.: PCT/IB2011/055569
§ 371 (c)(1),
(2), (4) Date: Jun. 11, 2013

(87) PCT Pub. No.: WO2012/080920
PCT Pub. Date: Jun. 21, 2012

(65) Prior Publication Data
US 2013/0267862 A1    Oct. 10, 2013

Related U.S. Application Data (60) Provisional application No. 61/424,152, filed on Dec. 17, 2010.

(51) Int. Cl.
*A61B 5/08* (2006.01)
*A61B 5/083* (2006.01)
(Continued)

(52) U.S. Cl.
CPC ........... *A61B 5/0816* (2013.01); *A61B 5/082* (2013.01); *A61B 5/0836* (2013.01);
(Continued)

(58) Field of Classification Search
USPC ...................................................... 600/485
See application file for complete search history.

(56) References Cited

U.S. PATENT DOCUMENTS

| | | | | |
|---|---|---|---|---|
| 2,831,181 A | * | 4/1958 | Warner | A61B 5/0816 340/595 |
| 5,339,818 A | * | 8/1994 | Baker | A61B 5/02156 128/925 |

(Continued)

FOREIGN PATENT DOCUMENTS

| | | |
|---|---|---|
| CN | 101125084 A | 2/2008 |
| CN | 101794357 A | 8/2010 |

(Continued)

OTHER PUBLICATIONS

Agatonovic-Kustrin, S., and R. Beresford. "Basic concepts of artificial neural network (ANN) modeling and its application in pharmaceutical research." Journal of pharmaceutical and biomedical analysis 22.5 (2000): 717-727.*

*Primary Examiner* — Rajeev P Siripurapu
*Assistant Examiner* — Jairo H Portillo
(74) *Attorney, Agent, or Firm* — Daniel H. Brean (57) ABSTRACT

A system is configured to determine one or more breathing parameters of a subject, such as one or both of end-tidal carbon dioxide concentration and/or breath rate. The system is configured to make a plurality of preliminary determinations of an individual breathing parameter according to a plurality of different algorithms. A final determination of the breathing parameter is obtained by selecting one of the preliminary determinations based on therapy parameters, gas parameters, and/or other parameters that impact the accuracy and/or precision of the different algorithms.

17 Claims, 2 Drawing Sheets

(51) Int. Cl.
*G16H 20/00* (2018.01)
*G16H 40/60* (2018.01)
*A61B 5/00* (2006.01)

(52) U.S. Cl.
CPC .......... *A61B 5/4836* (2013.01); *A61B 5/7203* (2013.01); *G16H 20/00* (2018.01); *G16H 40/60* (2018.01)

(56) References Cited

U.S. PATENT DOCUMENTS

| | | | | |
|---|---|---|---|---|
| 5,777,735 | A * | 7/1998 | Reagen | G01J 3/453 356/244 |
| 6,887,208 | B2 | 5/2005 | Kushnir et al. | |
| 7,798,963 | B2 | 9/2010 | White et al. | |
| 8,660,971 | B2 | 2/2014 | Orr | |
| 2002/0023644 | A1* | 2/2002 | Berthon-Jones | A61B 5/085 128/204.22 |
| 2002/0110849 | A1* | 8/2002 | Leonhardt | A61B 5/0836 435/40.5 |
| 2004/0004056 | A1 | 1/2004 | Araki et al. | |
| 2004/0012927 | A1 | 1/2004 | Lee et al. | |
| 2004/0040560 | A1* | 3/2004 | Euliano | A61B 5/08 128/204.23 |
| 2004/0129271 | A1* | 7/2004 | Hickle | G06F 19/3456 128/204.23 |
| 2004/0171956 | A1* | 9/2004 | Babashan | A61B 5/02438 600/509 |
| 2005/0020886 | A1 | 1/2005 | Hutchinson et al. | |
| 2005/0020952 | A1 | 1/2005 | McCarthy et al. | |
| 2005/0080461 | A1* | 4/2005 | Stahmann | A61B 5/0031 607/17 |
| 2005/0209521 | A1* | 9/2005 | Kettunen | A61B 5/0205 600/508 |
| 2006/0111933 | A1* | 5/2006 | Wheeler | G06F 19/345 705/2 |
| 2007/0043300 | A1* | 2/2007 | Koblanski | A61B 5/0205 600/527 |
| 2008/0000490 | A1 | 1/2008 | Jo | |
| 2008/0139955 | A1* | 6/2008 | Hansmann | A61B 5/0816 600/529 |
| 2008/0171945 | A1 | 7/2008 | Dotter | |
| 2008/0214903 | A1 | 9/2008 | Obach | |
| 2008/0275349 | A1* | 11/2008 | Halperin | A61B 5/0205 600/484 |
| 2009/0018409 | A1* | 1/2009 | Banet | A61B 5/0408 600/301 |
| 2009/0024195 | A1 | 1/2009 | Deogaonkar et al. | |
| 2009/0241955 | A1* | 10/2009 | Jafari | A61M 16/0051 128/204.23 |
| 2009/0326383 | A1* | 12/2009 | Barnes | A61B 5/0059 600/476 |
| 2010/0152600 | A1* | 6/2010 | Droitcour | A61B 5/05 600/534 |
| 2010/0179392 | A1* | 7/2010 | Chang | A61B 5/0205 600/301 |
| 2011/0019064 | A1 | 1/2011 | Stallinga | |
| 2011/0190643 | A1* | 8/2011 | Zhang | A61B 5/021 600/486 |
| 2013/0267862 | A1 | 10/2013 | Jaffe et al. | |

FOREIGN PATENT DOCUMENTS

| | | | |
|---|---|---|---|
| WO | 2005034001 | A1 | 4/2005 |
| WO | 2008108849 | A1 | 9/2008 |
| WO | WO-2010044040 | A1 * | 4/2010 ............ G06F 19/00 |

* cited by examiner

SYSTEM AND METHOD FOR DETERMINING ONE OR MORE BREATHING PARAMETERS OF A SUBJECT

BACKGROUND

1. Field of the Disclosure

The invention relates to the determination of end-tidal carbon dioxide concentration and/or breath rate.

2. Description of the Related Art

Systems configured to determine breathing parameters of a subject, such as end-tidal carbon dioxide concentration and breath rate are known. Typically these systems implement a single algorithm for determining a given breathing parameter based on the output signals of a gas sensor in communication with gas at or near the airway of the subject. These algorithms generally provide enhanced precision and/or accuracy under some conditions, while producing somewhat marginal results under other conditions. As a result, use of conventional systems for determining breathing parameters may produce results having accuracy and/or precision that is not consistent for a variety of conditions.

SUMMARY

One aspect of this disclosure relates to a system configured to determine a breathing parameter of a subject receiving therapy. In one embodiment, the system comprises one or more sensors and one or more processors. The one or more sensors are configured to generate output signals conveying information related to one or more gas parameters of the gas at or near the airway of the subject. The one or more processors are configured to execute modules including a therapy parameter module, a breathing parameter module, and a selection module. The therapy parameter module is configured to determine one or more parameters of the therapy being provided to the subject. The breathing parameter module is configured to determine a breathing parameter of the respiration of the subject, and includes a first breathing parameter sub-module and a second breathing parameter sub-module. The first breathing parameter sub-module is configured to make a first determination of the breathing parameter based on the output signals in accordance with a first algorithm. The second breathing parameter sub-module is configured to make a second determination of the breathing parameter based on the output signals in accordance with a second algorithm, wherein an impact of the one or more therapy parameters on the accuracy and/or precision of the first algorithm is different than an impact of the one or more therapy parameters on the accuracy and/or precision of the second algorithm. The selection module is configured to select the first determination of the breathing parameter or the second determination of the breathing parameter as a final determination of the breathing parameter based on the one or more parameters of the therapy being provided to the subject.

Another aspect of this disclosure relates to a method of determining a breathing parameter of a subject receiving therapy. In one embodiment, the method comprises generating output signals conveying information related to one or more gas parameters of the gas at or near the airway of the subject; determining one or more parameters of the therapy being provided to the subject; making a first determination of a breathing parameter based on the output signals in accordance with a first algorithm; making a second determination of the breathing parameter based on the output signals in accordance with a second algorithm that is different from the first algorithm, wherein an impact of the one or more therapy parameters on the accuracy and/or precision of the first algorithm is different than an impact of the one or more therapy parameters on the accuracy and/or precision of the second algorithm; and selecting the first determination of the breathing parameter or the second determination of the breathing parameter as a final determination of the breathing parameter based on the one or more parameters of the therapy being provided to the subject.

Yet another aspect of the disclosure relates to a system for determining a breathing parameter of a subject receiving therapy. In one embodiment, the system comprises means for generating output signals conveying information related to one or more gas parameters of the gas at or near the airway of the subject; means for determining one or more parameters of the therapy being provided to the subject; means for making a first determination of a breathing parameter based on the output signals in accordance with a first algorithm; means for making a second determination of the breathing parameter based on the output signals in accordance with a second algorithm that is different from the first algorithm, wherein an impact of the one or more therapy parameters on the accuracy and/or precision of the first algorithm is different than an impact of the one or more therapy parameters on the accuracy and/or precision of the second algorithm; and means for selecting the first determination of the breathing parameter or the second determination of the breathing parameter as a final determination of the breathing parameter based on the one or more parameters of the therapy being provided to the subject.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment, the structural components illustrated herein are drawn to scale. It is to be expressly understood, however, that the drawings are for the purpose of illustration and description only and are not a limitation. In addition, it should be appreciated that structural features shown or described in any one embodiment herein can be used in other embodiments as well. It is to be expressly understood, however, that the drawings are for the purpose of illustration and description only and are not intended as a definition of limits. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
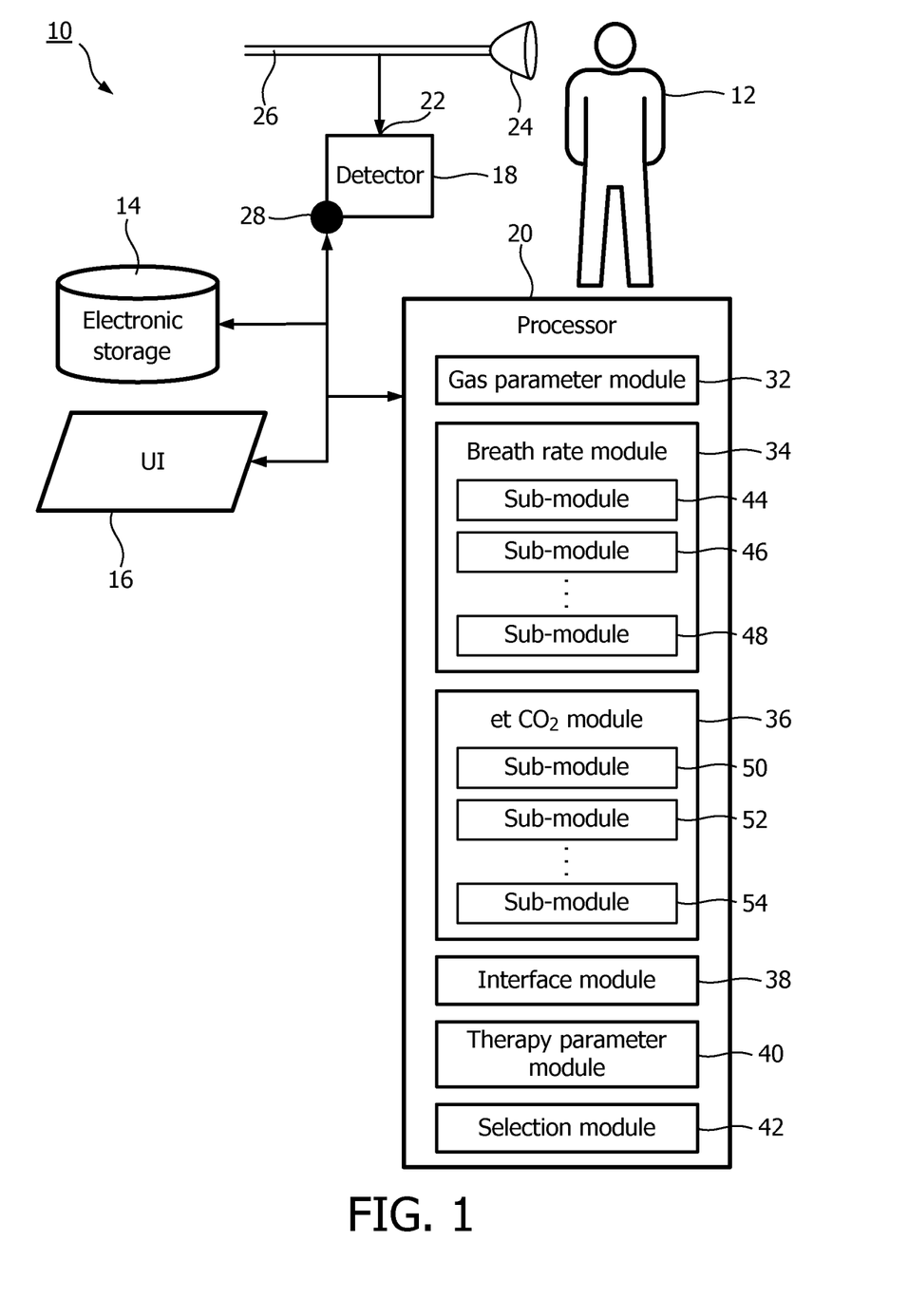
FIG. 1 illustrates a system configured to determine one or more breathing parameters of a subject.

FIG. 1 illustrates a system 10 configured to determine one or more breathing parameters of a subject 12. In some of the examples described below the one or more breathing parameters include one or both of end-tidal carbon dioxide concentration and/or breath rate. It will be appreciated that these examples are not intended to be limiting and the scope of this disclosure includes other breathing parameters. In particular, system 10 is configured to make a plurality of preliminary determinations of an individual breathing parameter according to a plurality of different algorithms. A final determination of the breathing parameter is obtained by selecting one of the preliminary determinations based on therapy parameters, gas parameters, and/or other parameters that impact the accuracy and/or precision of the different algorithms. In one embodiment, system 10 includes electronic storage 14, a user interface 16, a detector system 18, a processor 20, and/or other components.

In one embodiment, electronic storage 14 comprises electronic storage media that electronically stores information. The electronic storage media of electronic storage 14 may include one or both of system storage that is provided integrally (La, substantially non-removable) with system 10 and/or removable storage that is removably connectable to system 10 via, for example, a port (e.g., a USB port, a firewire port, etc.) or a drive (e.g., a disk drive, etc.). Electronic storage 14 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 14 may store software algorithms, information determined by processor 20, information received via user interface 16, and/or other information that enables system 10 to function properly. Electronic storage 14 may be a separate component within system 10, or electronic storage 14 may be provided integrally with one or more other components of system 10 (e.g., processor 20).

User interface 16 is configured to provide an interface between system 10 and a user (e.g., the user, a caregiver, a therapy decision-maker, etc.) through which the user may provide information to and receive information from system 10. This enables data, results, and/or instructions and any other communicable items, collectively referred to as "information," to be communicated between the user and system 10. Examples of interface devices suitable for inclusion in user interface 16 include a keypad, buttons, switches, a keyboard, knobs, levers, a display screen, a touch screen, speakers, a microphone, an indicator light, an audible alarm, and a printer.

It is to be understood that other communication techniques, either hard-wired or wireless, are also contemplated by the present invention as user interface 16. For example, in one embodiment, user interface 16 may be integrated with a removable storage interface provided by electronic storage 14. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 16 include, but are not limited to, an RS-232 port, RF link, an IR link, modem (telephone, cable or other). In short, any technique for communicating information with system 10 is contemplated as user interface 16.

The detector system 18 is configured to obtain gas from at or near the airway of subject 12, and to generate output signals conveying information obtained from measurements taken from the obtained gas. The detector system 18 is configured to receive gas obtained at or near the airway of subject 12 via an inlet 22. The gas is conveyed to inlet 22 by way of a subject interface appliance 24 and/or a conduit 26. The subject interface appliance 24 may engage one or more orifices of the airway of subject 12 in a sealed or unsealed manner. Some examples of subject interface appliance 24 may include, for example, an endotracheal tube, a nasal cannula, a tracheotomy tube, a nasal mask, a nasal/oral mask, a full face mask, a total face mask, a partial rebreathing mask, or other interface appliances that communicate a flow of gas with an airway of a subject. The present invention is not limited to these examples, and contemplates implementation of any subject interface.

The conduit 26 is configured to place inlet 22 of detector system 18 in fluid communication with subject interface appliance 24 such that gas obtained by subject interface appliance 24 from at or near the airway of subject 12 is provided to inlet 22 via conduit 26. In one embodiment, detector system 18 is configured for sidestream sampling. In this configuration, conduit 26 is further configured to place subject interface appliance 24 in fluid communication with a source of a breathable substance. For example, a flow of breathable gas may be delivered to subject 12 through conduit 26 having one or more parameters that are controlled in accordance with a therapy regime. The one or more parameters of the flow of breathable gas that are controlled may include one or more of pressure, flow, composition, humidity, temperature, and/or other parameters. In one embodiment, detector system 18 is configured for mainstream sampling. In this configuration, detector system 18 is disposed within the flow path through conduit 26, rather than being disposed off to the side (as is shown in FIG. 1). In one embodiment in which detector system 18 configured for sidestream sampling, or in which conduit 26 does not provide for provision of a breathable substance to the airway of subject 12, a pump (not shown) is configured to draw gas from conduit 26 into detector system 18 through inlet 22.

The detector system 18 includes one or more sensors 28. The sensors 28 are configured to generate output signals conveying information related to one or more gas parameters of the gas within detector system 18. The one or more gas parameters may include one or more of concentration of a gaseous molecular species (e.g., carbon dioxide, oxygen, and/or other molecular species), a flow, a pressure, a temperature, a humidity, and/or other gas parameters. It will be appreciated that the illustration of sensors 28 in FIG. 1 as an individual component within detector system 18 is not intended to be limiting. In one embodiment, sensors 28 can be a single sensor, or may include a plurality of sensors.

Processor 20 is configured to provide information processing capabilities in system 10. As such, processor 20 may include one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may include a plurality of processing units. These processing units may be physically located within the same device, or processor 20 may represent processing functionality of a plurality of devices operating in coordination.

As is shown in FIG. 1, processor 20 may be configured to execute one or more computer program modules. The one or more computer program modules may include one or more of a gas parameter module 32, a breath rate module 34, an end-tidal carbon dioxide module 36, an interface module 38, a therapy parameter module 40, a selection module 42, and/or other modules. Processor 20 may be configured to execute modules 32, 34, 36, 38, 40, and/or 42 by software; hardware; firmware; some combination of software, hardware, and/or firmware; and/or other mechanisms for configuring processing capabilities on processor 20.

It should be appreciated that although modules 32, 34, 36, 38, 40, and/or 42 are illustrated in FIG. 1 as being co-located within a single processing unit, in implementations in which processor 20 includes multiple processing units, one or more of modules 32, 34, 36, 38, 40, and/or 42 may be located remotely from the other modules. The description of the functionality provided by the different modules 32, 34, 36, 38, 40, and/or 42 described below is for illustrative purposes, and is not intended to be limiting, as any of modules 32, 34, 36, 38, 40, and/or 42 may provide more or less functionality than is described. For example, one or more of modules 32, 34, 36, 38, 40, and/or 42 may be eliminated, and some or all of its functionality may be provided by other ones of modules 32, 34, 36, 38, 40, and/or 42. As another example, processor 20 may be configured to execute one or more additional modules that may perform some or all of the functionality attributed below to one of modules 32, 34, 36, 38, 40, and/or 42.

The gas parameter module 32 is configured to determine one or more gas parameters of gas at or near the airway of subject 12 based on the output signals generated by sensors 28. The one or more gas parameters may include one or more of concentration of a gaseous molecular species (e.g., carbon dioxide, oxygen, and/or other molecular species), a flow, a pressure, a temperature, a humidity, and/or other gas parameters.

The breath rate module 34 is configured to determine a breath rate of subject 12. The breath rate module 34 includes a first breath rate sub-module 44, a second breath rate sub-module 46, an nth breath rate sub-module 48, and/or other sub-modules. The individual sub-modules 44, 46, and 48 are configured to determine the breath rate of subject 12 based on the output signals generated by sensors 28 and/or the gas parameters determined by gas parameter module 32. Each of the individual sub-modules 44, 46, and 48 is configured to determine the breath rate according to a different algorithm than the other sub-modules 44, 46, and 48. Each of the different algorithms is impacted differently with respect to accuracy and/or precision by various conditions. For example, under a first set of conditions, determination of breath rate by second breath rate sub-module 46 may be more accurate and/or precise than determination of breath rate by nth breath rate sub-module 48. But under a second set of conditions, the determination of breath rate by nth breath rate sub-module 48 may be accurate and/or precise than determination of breath rate by second breath rate sub-module 46.

Differences in conditions may be described by, for example, therapy parameters related to therapy being administered to subject 12. The therapy parameters may include one or more of a current therapeutic procedure, a current therapy device, a context in which therapy is being delivered, a subject parameter, and/or other therapy parameters. Parameters describing a current therapeutic procedure may describe, for example, invasive ventilation, non-invasive ventilation, cardiopulmonary resuscitation, procedural sedation, and/or other procedures. Parameters describing a context in which therapy is being delivered may describe, for example the emergency state, clinical situation (e.g., intensive care, operation underway, emergency vehicle), and/or other contextual parameters. Subject parameters may describe one or more aspects of subject 12 (e.g., age, weight, height, blood pressure, pulse rate, pre-existing conditions, and/or other aspects).

The end-tidal carbon dioxide module 36 is configured to determine an end-tidal carbon dioxide concentration of subject 12. The end-tidal carbon dioxide module 36 includes a first end-tidal carbon dioxide sub-module 50, a second end-tidal carbon dioxide sub-module 52, an nth end-tidal carbon dioxide sub-module 54, and/or other sub-modules. The individual sub-modules 50, 52, and 54 are configured to determine the end-tidal carbon dioxide concentration of subject 12 based on the output signals generated by sensors 28 and/or the gas parameters determined by gas parameter module 32. Each of the individual sub-modules 50, 52, and 54 is configured to determine the end-tidal carbon dioxide concentration according to a different algorithm than the other sub-modules 50, 52, and 54. Each of the different algorithms is impacted differently with respect to accuracy and/or precision by various conditions. The conditions may be described by therapy parameters such as those described above.

The interface module 38 is configured to receive input from a user (e.g., a caregiver, a therapy provider, a researcher, subject 12, and/or other users) related to one or more therapy parameters. In one embodiment, interface module 38 is configured to receive a definition of a therapy parameter. For example, interface module 38 may be configured to receive a definition of a current therapeutic procedure, a current therapy device, a context in which therapy is being delivered, a subject parameter, and/or other therapy parameters. Input from the user may be received by interface module 38 via user interface 16.

The therapy parameter module 40 is configured to determine one or more therapy parameters automatically. For example, system 10 may include one or more sensors (not shown) configured to generate output signals indicating information related to one or more of a current therapeutic procedure, a current therapy device, a context in which therapy is being delivered, a subject parameter, and/or other therapy parameters. The therapy parameter module 40 is configured to automatically determine definitions of one or more therapy parameters from these output signals. The therapy parameters may include gas parameters of the pressurized flow of breathable gas taken by sensors other than sensor 28. For example, a pressure sensor and/or a flow sensor included in detector 18 and/or associated with a pressure generator (not shown, e.g., a ventilator) may generate output signals conveying information related to gas parameters of the pressurized flow of breathable gas that are not implemented by any of sub-modules 44, 46, 48, 50, 52, and/or 54. These gas parameters may provide information about the therapy and/or the subject even though they are not implemented in the determination of the breathing parameter.

The selection module 42 is configured to select between sub-modules of a given breathing parameter module based on the one or more therapy parameters defined via user input and/or via automatic determination by therapy parameter module 40. The selection module 42 may select between sub-modules to enhance the accuracy and/or precision of a final determination of the breathing parameter under the current conditions defined by the one or more therapy parameters. The selection may include selecting a set of sub-modules to make preliminary determinations of the breathing parameter and/or selecting a final determination of the breathing parameter from a set of preliminary determinations.

For example, with respect to breath rate module 34, selection module 42 may be configured to select a set of sub-modules 44, 46, and/or 48 to make preliminary determinations of breath rate. The determination of which of the sub-modules 44, 46, and/or 48 should make preliminary determinations of breath rate can be made based on therapy parameters such that the set of sub-modules 44, 46, and 48 that make preliminary determinations are the sub-modules implementing the algorithms that tend to enhance accuracy and/or precision under the conditions defined by the current therapy parameters. It will be appreciated that selection of a set of sub-modules 44, 46, and/or 48 to make preliminary determinations of breath rate is not intended to be limiting. In one embodiment, all of the sub-modules 44, 46, and 48 are implemented to make preliminary determinations.

The selection module 42 may be configured to select a final determination of breath rate from the preliminary determinations of breath rate. The selection module 42 may make this selection based on one or more therapy parameters and/or the preliminary determinations themselves. Selection may be based on analysis of the preliminary determinations to identify artifacts commonly indicative of inaccuracy and/or imprecision. The identification of such artifacts in preliminary determination of the breath rate by selection module 42 may be facilitated by looking for artifacts sometimes or commonly present in determination of breath rate by a given breath rate algorithm used to make the preliminary determination being analyzed. The identification of such artifacts may be further enhanced or fine-tuned by looking for one or more artifacts commonly present under the present conditions (as described by the therapy parameters). Other dependence on the therapy parameters and/or the preliminary determinations are contemplated.

In one embodiment, selection module 42 is configured to determine a reliability metric indicating the reliability of one or more of the preliminary determinations. Such a metric determined for a preliminary determination may reflect signal stability, a rate of change, a trend, a noise level, appropriateness of the data for the size patient (if the patient is neonatal or pediatric, the expected measurement will be difference than is expected for an adult patient) and/or other features of the preliminary determination that indicate whether the preliminary determination is accurate and/or precise. For example, if the preliminary determination is determined to fluctuate over time, this may indicate noise present in the preliminary determination that reduces the reliability of the determination. The reliability metric for the noisy preliminary determination would reflect this noise.

The selection module 42 may further be configured to base the selection of a preliminary determination on analysis of the therapy parameters in conjunction with the reliability metric(s) determined for the individual preliminary determinations. Responsive to the reliability metric(s) determined for a given preliminary determination indicating a relatively low reliability (e.g., due to noise and/or other phenomena), the given preliminary determination may not be selected as the final determination. Similarly, responsive to the reliability metric(s) determined for the given preliminary determination indicating a relatively high reliability, the given preliminary determination may be given priority over other preliminary determinations with lower reliability.

With respect to end-tidal carbon dioxide module 36, selection module 42 may be configured to select a set of sub-modules 50, 52, and 54 to make preliminary determinations of end-tidal carbon dioxide concentration, and/or to select final determination of end-tidal carbon dioxide concentration from preliminary determinations of end-tidal carbon dioxide concentration made by sub-modules 50, 52, and/or 54. The selection of the set of sub-modules 50, 52, and/or 52 to make preliminary determinations, and/or the selection of a final determination of end-tidal carbon dioxide concentration may be made based on one or more therapy parameters and/or reliability metrics to enhance the accuracy and/or precision of end-tidal carbon dioxide concentration determination under the present conditions. The selection may be performed similar to or the same as described above with respect to selection(s) of breath rate determinations made by selection module 42.

Figure 2:
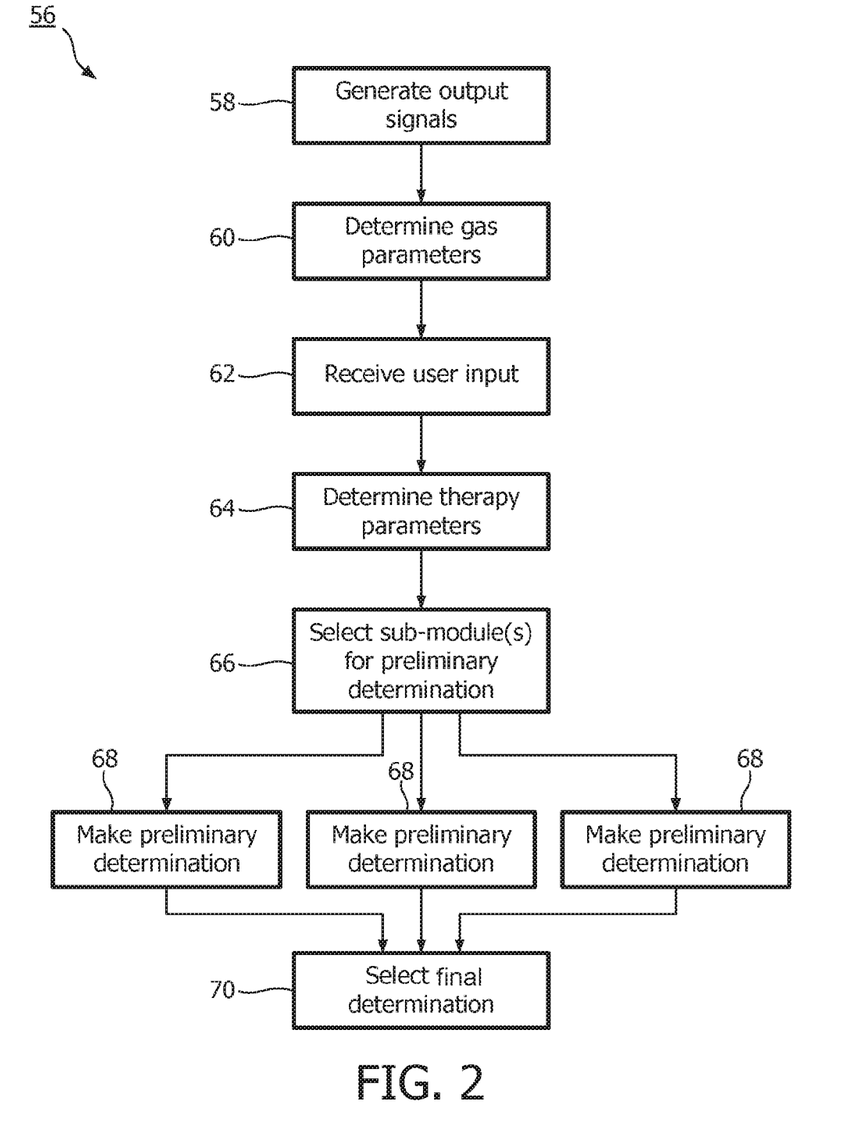
FIG. 2 illustrates a method of determining a breathing parameter of a subject.

FIG. 2 illustrates a method 56 of determining a breathing parameter of a subject. The operations of method 56 presented below are intended to be illustrative. In some embodiments, method 56 may be accomplished with one or more additional operations not described, and/or without one or more of the operations discussed. Additionally, the order in which the operations of method 56 are illustrated in FIG. 2 and described below is not intended to be limiting.

In some embodiments, method 56 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 56 in response to instructions stored electronically on an electronic storage medium. The one or more processing devices may include one or more devices configured through hardware, firmware, and/or software to be specifically designed for execution of one or more of the operations of method 56.

At an operation 58, output signals conveying information related to one or more gas parameters of the gas at or near the airway of a subject are generated. The one or more gas parameters may include one or more of concentration of a gaseous molecular species (e.g., carbon dioxide, oxygen, and/or other molecular species), a flow, a pressure, a temperature, a humidity, and/or other gas parameters. In one embodiment, operation 58 is performed by one or more sensors that is the same as, or similar to, sensors 28 (shown in FIG. 1 and described above).

At an operation 60, one or more gas parameters of the gas at or near the airway of the subject are determined based on the output signals generated at operation 58. In one embodiment, operation 60 is performed by a gas parameter module that is the same as, or similar to, gas parameter module 32 (shown in FIG. 1 and described above).

At an operation 62, input related to one or more therapy parameters may be received from a user. In one embodiment, operation 62 is performed by an interface module that is the same as, or similar to, interface module 38 (shown in FIG. 1 and described above).

At an operation 64, one or more therapy parameters are determined. The one or more therapy parameters may include one or more of a current therapeutic procedure, a current therapy device, a context in which therapy is being delivered, a subject parameter, and/or other therapy parameters. The determined one or more therapy parameters describe the current conditions under which the breathing parameter is being determined. The one or more therapy parameters may be determined based on user input received at operation 62, from output signals of sensors conveying information related to the therapy parameter(s), and/or determined based on other information. In one embodiment, operation 64 is performed by a therapy parameter module that is the same as, or similar to, therapy parameter module 40 (shown in FIG. 1 and described above).

At an operation 66, a set of sub-modules are selected to make preliminary determinations of the breathing parameter. The sub-modules each implement a separate algorithm for determining the breathing parameter as a function of the output signals generated at operation 58 and/or the gas parameters determined at operation 60. The accuracy and/or the precision of the different algorithms in determining the breathing parameter are impacted differently by the therapy parameters. The selection of the set of sub-modules at operation 66 from a larger group of sub-modules selects the sub-modules implementing the algorithms that typically have an enhanced accuracy and/or precision under the conditions described by the therapy parameters determined at operation 68. In one embodiment, operation 66 is performed by a selection module that is the same as, or similar to, selection module 42 (shown in FIG. 1 and described above). Selection of the set of sub-modules may include selection from among a group of sub-modules that is the same as, or similar to, the group of sub-modules 44, 46, and 48 (shown in FIG. 1 and described above), and/or that is the same as, or similar to, the group of sub-modules 50, 52, and 54 (shown in FIG. 1 and described above).

At an operation 68, preliminary determinations of the breathing parameter are made based on the output signals generated at operation 58 and/or the gas parameters determined at operation 60. The preliminary determinations are made by the set of sub-modules selected at operation 66.

At an operation 70, final determination of the breathing parameter is selected from the preliminary determinations of the breathing parameter made at operation 68. Selection of the final determination of the breathing parameter is made based on the therapy parameters determined at operation 64, the preliminary determinations of the breathing parameter themselves, the gas parameters determined at operation 60, and/or based on other information. The selection of the final determination of the breathing parameter is made to select the preliminary determination of the breathing parameter typically having an enhanced accuracy and/or precision under the current conditions. Operation 70 may include the determination of one or more reliability metrics for individual ones of the preliminary determinations. The reliability metric(s) determined for a given preliminary determination may indicate the reliability of the given preliminary determination. The reliability metric(s) may reflect a rate of change, a trend, a noise level, and/or other features of the preliminary determination that indicate whether a given preliminary determination is accurate and/or precise. Selection of the final determination at operation 70 may be further based on the determined reliability metric(s) in conjunction with the other considerations listed above. In one embodiment, operation 70 is performed by a selection module that is the same as, or similar to, selection module 42 (shown in FIG. 1 and described above).

Details included herein are for the purpose of illustration based on what is currently considered to be the most practical and preferred embodiments, it is to be understood that such detail is solely for that purpose and that the scope of this specification is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to determine a breathing parameter of a subject receiving therapy, wherein the breathing parameter is one of end-tidal carbon dioxide concentration or breath rate, the system comprising:
   one or more sensors configured for placement at an airway of the subject to obtain and measure gas at the airway of the subject and configured to generate, based on the measurement of the gas, output sensor signals conveying information related to one or more gas parameters during a first time period, the one or more gas parameters including one or more of concentration of one or more gaseous molecular species, a flow, a pressure, a temperature, or a humidity of the measured gas; and
   one or more hardware processors configured by machine-readable instructions to:
      determine parameters of the therapy being provided to the subject;
      determine a breathing parameter of the respiration of the subject with respect to the first time period by:
         receiving a first preliminary determination of the breathing parameter from an associated first breath rate sub-module that determines the breathing parameter using a first algorithm based on the output sensor signals generated during the first time period and a first set of the therapy parameters;
         receiving a second preliminary determination of the breathing parameter from an associated second breath rate sub-module that determines the breathing parameter using a second algorithm based on the output sensor signals generated during the first time period and a second set of the therapy parameters, wherein an impact of the first set of the therapy parameters on the accuracy and/or precision of making the first preliminary determination is different than an impact of the second set of the therapy parameters on the accuracy and/or precision of making the second preliminary determination;
         determining a noise-based reliability metric for each of the first and second preliminary determinations of the breathing parameter that indicate reliability; and
         selecting (a)(i) the first preliminary determination of the breathing parameter or (a)(ii) the second preliminary determination of the breathing parameter as a final determination of the breathing parameter (b) based at least on the determined noise-based reliability metrics for the first and second preliminary determinations of the breathing parameter; and
      control a ventilator based on the determined breathing parameter.

2. The system of claim 1, wherein the therapy parameters comprise one or more of a current therapeutic procedure, a current therapy delivery device, or a context in which therapy is being delivered.

3. The system of claim 1, wherein the breathing parameter is end-tidal carbon dioxide concentration.

4. The system of claim 1, wherein the breathing parameter is breath rate.

5. The system of claim 1, wherein the one or more hardware processors are configured by machine-readable instructions to determine the therapy parameters, wherein the therapy parameters comprise determining gas parameters of a pressurized flow of gas.

6. The system of claim 1, wherein the therapy parameters comprise all of a current therapeutic procedure, a current therapy delivery device, and a context in which therapy is being delivered.

7. The system of claim 1, wherein the therapy parameters comprise subject parameters including all of an age, a weight, a height, a blood pressure, a pulse rate, and a pre-existing condition of the subject.

8. The system of claim 1, further comprising a user interface including a display configured to display the selected preliminary determination of the breathing parameter.

9. A method of determining a breath rate of a subject receiving therapy with a system including one or more sensors and one or more hardware processors, the method comprising:
 generating, with the one or more sensors, output sensor signals conveying information related to one or more gas parameters during a first time period, the one or more sensors configured for placement at an airway of the subject to obtain and measure gas at the airway of the subject, the output sensor signals based on the measurement of the gas, the one or more gas parameters including at least one of concentration of one or more gaseous molecular species, a flow, or a pressure; and
 determining, with the one or more hardware processors, parameters of the therapy being provided to the subject;
 receiving, with the one or more hardware processors, a first preliminary determination of the breath rate from an associated first breath rate sub-module that determines the breathing parameter using a first algorithm based on the output sensor signals generated during the first time period and a first set of the therapy parameters;
 receiving, with the one or more hardware processors, a second preliminary determination of the breath rate from an associated second breath rate sub-module that determines the breathing parameter using a second algorithm based on the output sensor signals generated during the first time period and a second set of the therapy parameters, wherein an impact of the first set of the therapy parameters on the accuracy and/or precision of making the first preliminary determination is different than an impact of the second set of the therapy parameters on the accuracy and/or precision of making the second preliminary determination;
 selecting, using the one or more hardware processors, (a)(i) the first preliminary determination of the breath rate or (a)(ii) the second preliminary determination of the breath rate as a final determination of the breath rate (b) based on analysis of the first and second preliminary determinations to identify artifacts indicative of inaccuracy and/or imprecision in determination of a respective breath rate obtained from the first and second preliminary determinations, wherein the artifacts comprise artifacts commonly present under conditions described by the therapy parameters;
 determining a reliability metric for each of the first and second preliminary determinations of the breath rate that indicate reliability, and wherein the selection between the first and second preliminary determinations is further based on the determined reliability metrics for the first and second preliminary determinations of the breath rate; and
 controlling a ventilator based on the determined breath rate.

10. The method of claim 9, wherein the therapy parameters comprise one or more of a current therapeutic procedure, a current therapy delivery device, or a context in which therapy is being delivered.

11. The method of claim 9, wherein the determining the therapy parameters comprises determining gas parameters of a pressurized flow of gas.

12. The method of claim 9, wherein the reliability metric is a noise-based reliability metric.

13. A system for: (i) determining an end-tidal carbon dioxide concentration of a subject receiving therapy, and (ii) controlling a ventilator based on the determined end-tidal carbon dioxide concentration, the system comprising:
 one or more sensors for generating output sensor signals conveying information related to one or more gas parameters during a first time period, the one or more sensors being configured for placement at an airway of the subject to obtain and measure gas at the airway of the subject, the output sensor signals based on the measurement of the gas, the one or more gas parameters including at least concentration of carbon dioxide; and
 one or more hardware processors programmed to:
 determine parameters of the therapy being provided to the subject;
 receive a first preliminary determination of an end-tidal carbon dioxide concentration from an associated first sub-module that determines the end-tidal carbon dioxide concentration using a first algorithm based on the output sensor signals generated during the first time period and a first set of the therapy parameters;
 receive a second preliminary determination of the end-tidal carbon dioxide concentration from an associated second sub-module that determines the end-tidal carbon dioxide concentration using a second algorithm based on the output sensor signals generated during the first time period and a second set of the therapy parameters, wherein an impact of the first set of the therapy parameters on the accuracy and/or precision of making the first preliminary determination is different than an impact of the second set of the therapy parameters on the accuracy and/or precision of making the second preliminary determination; and
 select (a)(i) the first preliminary determination of the end-tidal carbon dioxide concentration or (a)(ii) the second preliminary determination of the end-tidal carbon dioxide concentration as a final determination of the end-tidal carbon dioxide concentration based on analysis of the first and second preliminary determinations to identify artifacts indicative of inaccuracy and/or imprecision in determination of a respective end-tidal carbon dioxide concentration obtained from the first and second preliminary determinations, wherein the artifacts comprise artifacts commonly present under conditions described by the therapy parameters.

14. The system of claim 13, wherein the one or more hardware processors are programmed to determine a reliability metric for each of the first and second preliminary determinations of the end-tidal carbon dioxide concentration that indicate reliability, and wherein the selection between the first and second preliminary determinations is further based on the determined reliability metrics for the first and second preliminary determinations of the end-tidal carbon dioxide concentration.

15. The system of claim 14, wherein the reliability metric is a noise-based reliability metric.

16. The system of claim 13, wherein the therapy parameters comprise one or more of a current therapeutic procedure, a current therapy delivery device, or a context in which therapy is being delivered.

17. The system of claim 13, wherein the one or more hardware processors are programmed to determine the therapy parameters by determining gas parameters of a pressurized flow of gas.

* * * * *